United States Patent [19]
Lin

[11] Patent Number: 5,466,238
[45] Date of Patent: Nov. 14, 1995

[54] VERTEBRAL LOCKING AND RETRIEVING SYSTEM HAVING A FIXATION CROSSBAR

[76] Inventor: Chih-I Lin, 513 S. Golden Pardos Dr., Diamond Bar, Calif. 10765

[21] Appl. No.: 361,480

[22] Filed: Dec. 22, 1994

Related U.S. Application Data

[63] Continuation of Ser. No. 112,517, Aug. 27, 1993, abandoned.

[51] Int. Cl.[6] ................................................... A61B 17/70
[52] U.S. Cl. ............................................................. 606/61
[58] Field of Search ................................. 606/61, 72, 73, 606/53, 54, 59, 60

[56] References Cited

U.S. PATENT DOCUMENTS

| | | | |
|---|---|---|---|
| 4,987,892 | 1/1991 | Krag et al. | 606/61 |
| 5,133,716 | 7/1992 | Plaza | 606/61 |
| 5,176,678 | 1/1993 | Tsou | 606/61 |
| 5,176,679 | 1/1993 | Lin | 606/61 |
| 5,196,013 | 3/1993 | Harms et al. | 606/61 |
| 5,196,014 | 3/1993 | Lin | 606/61 |

*Primary Examiner*—Tamara L. Graysay
*Attorney, Agent, or Firm*—Bacon & Thomas

[57] ABSTRACT

A vertebral locking and retrieivng system comprises two fixing screws, one fixation crossbar and a plurality of fasteners. Each of the two fixing screws is composed of a horizontal fixing portion and a threaded portion which is fastened onto a vertebra. The fixation crossbar is composed of a bar portion and at least one longitudinal fixing portion located at the midpoint of the bar portion. The horizontal fixing portions of the two fixing screws are fastened respectively with both ends of the bar portion of the fixaton crossbar by means of a plurality of fasteners. The threaded portion and the horizontal fixing portion of the fixing screw form an angle ranging between 3 degrees and 30 degrees. The two fixing screws are fastened onto the same vertebra such that they are opposite to each other.

11 Claims, 1 Drawing Sheet

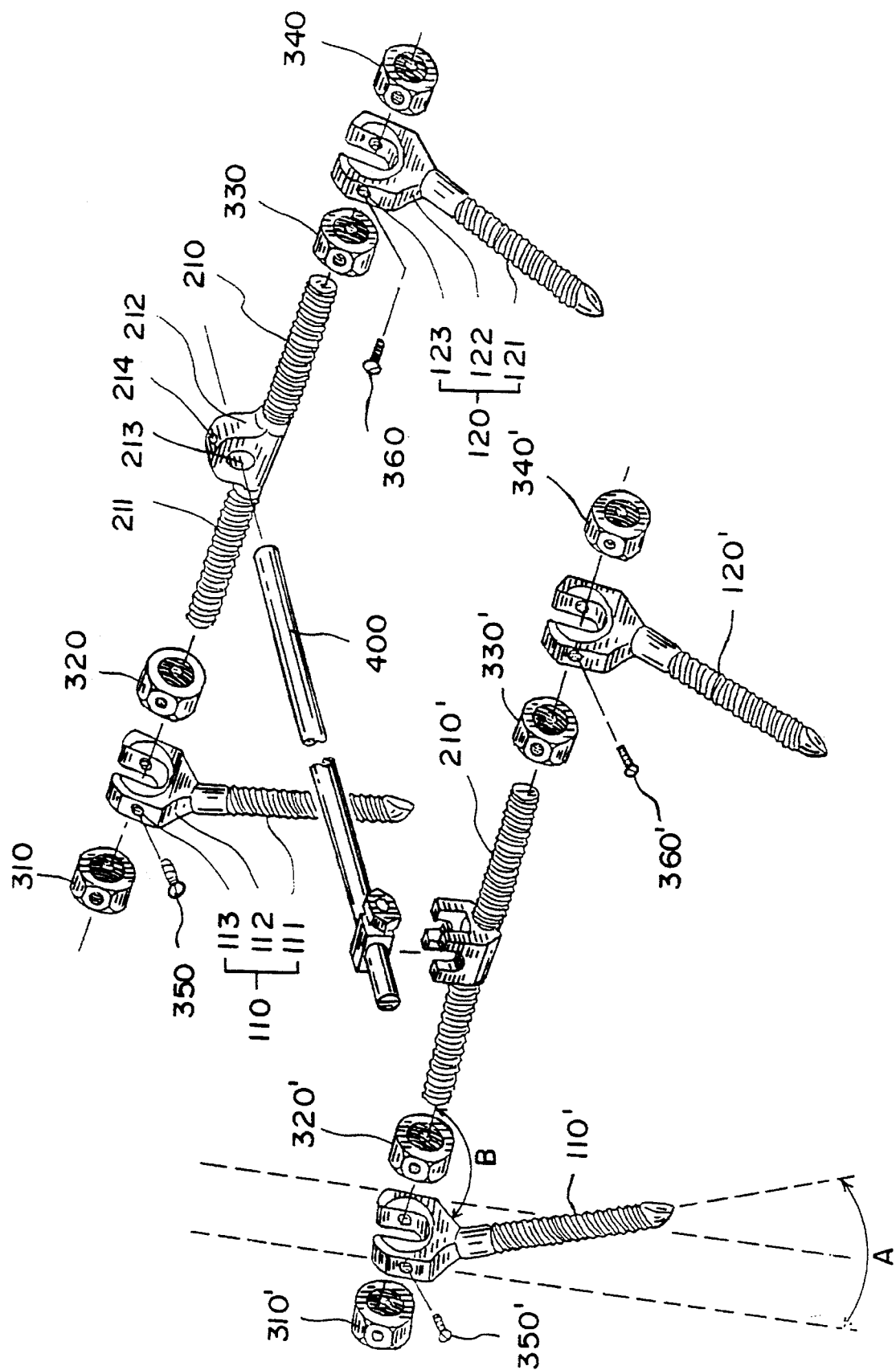

VERTEBRAL LOCKING AND RETRIEVING SYSTEM HAVING A FIXATION CROSSBAR

This application is a Continuation of application Ser. No. 08/112,517, filed Aug. 27, 1993, now abandoned.

FIELD OF THE INVENTION

The present invention relates to a vertebral locking and retrieving system having a fixation crossbar.

BACKGROUND OF THE INVENTION

General speaking, a conventional vertebral locking and retrieving screw is defective in design in that it is devoid of a specific angle capable of negotiating with the specific curvature of a vertebra. With a view to overcoming the defect of such a conventional bone screw as mentioned above, the inventor of the present invention discloses a variety of angled screws for use in locking and retrieving various vertebrae of the human spinal column, as exemplified in the U.S. Pat. Nos. 5,176,679; 5,196,014; 5,257,994 and 5,330,474. These variously angled screws disclosed by this inventor of the present invention are constructed on the basis of the fact that the curvatures of various vertebrae of the human vertebral column differ from one another. However, in a surgical operation, two bone screws having respectively a specific angle are never fastened onto the same vertebra after the vertebra in question has been fixed horizontally. This is due to the fact that the traditional surgical operation requires that the vertebra under treatmnet must be first fixed longitudinally and then fixed horizontally by means of an auxiliary fixing device. The concept of fastening two bone screws, each of which has a specific angle, onto the same vertebra began to take shape only after a vertebral locking and retrieving system having a center rod was disclosed by this inventor of the present invention in U.S. Pat. No. 5,387,212. In other words, a horizontal fixation and a longitudinal fixation of a deformed vertebra are attained by means of two bone screws which have respectively a specific angle and are fastened onto the deformed vertebra in such a manner that the two bone screws in question are not parallel to each other. With a view to reinforcing the fixation of the vertebra under treatment, a fixation crossbar is used. Such fixation crossbar must have a specific curvature so that the fixation crossbar can cooperate well with the two angled bone screws. The technical problem that is derived from the above-mentioned U.S. Pat. No. 5,387,212 is that the fixaton crossbar must have a specific curvature.

SUMMARY OF THE INVENTION

It is therefore the primary objective of the present invention to provide an innovative and novel vertebral locking and retrieving system having a fixaton crossbar.

It is another objective of the present invention to provide the vertebral locking and retrieving system with two fixing screws having respectively a threaded portion and a horizontal fixing portion which have respectively a specific angle capable of cooperating with the fixation crossbar.

It is still another objective of the present invention to provide the vertebral locking and retrieving system with two fixing screws capable of being fastened onto the same vertebra in cooperation with the fixation crossbar of the system.

It is still another objective of the present invention to provide the vertebral locking and retrieving system with two fixing screws, a fixation crossbar and a plurality of fasteners.

In keeping with the principles of the present invention, the foregoing objectives of the present invention are attained by a vertebral locking and retrieving system which comprises two fixing screws, one fixation crossbar, and a plurality of fasteners. Each of the two fixing screws is composed of a threaded portion and a horizontal fixing portion. The threaded portion of the fixing screw is fastened onto a vertebra. The fixation crossbar is composed of a bar portion and at least one longitudinal fixing portion located at the midpoint of the bar portion. The horizontal fixing portions of the two fixing screws are fastened respectively with both ends of the bar portion of the fixation crossbar by means of a plurality of fasteners. The threaded portion and the horizontal fixing portion of the fixing screw form an angle ranging between 3 degrees and 30 degrees. The two fixing screws are fastened onto the same vertebra such that they are opposite to each other.

The foregoing objectives and features of the present invention can be more readily understood upon a thoughtful deliberation of the following detailed description of the present invention in conjunction with the accompanying drawing.

BRIEF DESCRIPTION OF THE DRAWING

FIG. 1 shows an exploded view of a preferred embodiment of the present invention.

DETAILED DESCRIPTION OF THE INVENTION

As shown in FIG. 1, the preferred embodiment of the present invention comprises two fixing screws 110 and 120, a fixation crossbar 210, and a plurality of fasteners 310, 320, 330, 340, 350 and 360. The fasteners 310, 320, 330 and 340 are nuts while the fasteners 350 and 360 are small screws. These fasteners are used to fasten the fixing screws 110 and 120 with both ends of the fixation crossbar 210. The fixing screw 110 is composed of a threaded portion 111, a horizontal fixing portion 112 and a small threaded hole 113 engageable with the fastener 350. Another fixing screw 120 is similarly composed of a threaded portion 121, a horizontal fixing portion 122 and a small threaded hole 123 engageable with the fastener 360. The threaded portions 111 and 121 of the fixing screws 110 and 120 are fastened onto the same vertebra. The fixation crossbar 210 has a bar portion 211 provided at the midpoint thereof with a longitudinal fixing portion 212 which is composed of a small threaded hole 214 and a through hole 213 dimensioned to fit over one end of a longitudinal fixation rod 400 intended for use in fastening longitudinally the two fixation crossbars 210 and 210' of the two systems of the present invention. One end of the longitudinal fixation rod 400 is fastened with the fixation crossbar 210 by means of a small screw (not shown in the drawing) engageable with the small threaded hole 214 of the fixation crossbar 210. Another end of the longitudinal fixation rod 400 is fastened to the fixation crossbar 210' by the three-point fastening method which is commonly used in the prior art. The definitions of all the numerals designating the component elements of the fixation crossbar 210' are similar to those of the fixation crossbar 210.

The most important features of the present invention is that the threaded portion and the horizontal fixing portion of each of the fixing screws form an angle A ranging between 3 degrees and 30 degrees, and that the two fixing screws fastened to both ends of the fixation crossbar are fastened onto the same vertebra in such a manner that the two fixing screws are opposite to each other. In addition, the horizontal fixing portion of each of the fixing screws and the bar portion of the fixation crossbar form an angle B substantially equal to 90°.

The threaded portion and the horizontal fixing portion of the fixing screw of the present invention may be made integrally, as suggested in the U.S. Pat. No. 5,176,679 granted to this inventor of the present invention, or made separately and then put together, as disclosed in this invention's U.S. Pat. Nos. 5,196,014; 5,257,994 and 5,330,474.

The bar portion and the longitudial fixing portion of the fixation crossbar of the present invention may be made integrally, as suggested in this inventor's U.S. Pat. No. 5,387,212, or made separately and then put together.

The fasteners of the present invention are similar in construction to those of the prior art.

The fixation crossbar of the present invention may have one or more (preferably not more than three) longitudinal fixing portions. It is conceivable that the longitudinal fixing rod must be equal in number to the longitudinal fixing portion of the fixation crossbar.

It is not necessary that the two fixing screws of the system of the present invention are fastened onto a vertebra intended to be fixed. The two fixing screws may be fastened onto the coccygeal vertebrae and then fastened with the fixation crossbar before one end of the longitudinal fixing rod is fastened to the longitudinal fixing portion of the fixation crossbar. Thereafter, the longitudinal fixing rod and the vertebra to be fixed can be connected by means of a prior art vertebral locking device, such as the LUGUE hook. Furthermore, the threaded portions of the two fixing screws are generally fastened onto the same vertebra such that the distance between the two threaded portions is smaller than the distance between the two horizontal fixing portions. However, the distance between the two threaded portions may be greater than the distance between the two horizontal fixing portions, if the two fixing screws are fastened onto the coccygeal vertebrae.

What is claimed is:

1. A vertebral locking and retrieving system comprising:
   first and second fixing screws, each of which is composed of a horizontal fixing portion and a threaded portion, said first and second fixing screws being adapted to be fastened onto a single vertebra;
   a first fixation crossbar including a bar portion and at least one longitudinal fixing portion located at a mid-section of said bar portion having both ends which are fastened respectively with said horizontal fixing portion of each of said first and second fixing screws; and
   first and second sets of fasteners for fastening respectively said horizontal fixing portion of said each of said first and second screws to said both ends of said bar portion of said first fixation crossbar;
   wherein said threaded portion and said horizontal fixing portion of said each of said first and second fixing screws form an angle ranging between 3 degrees and 30 degrees, and the threaded portions of said first and second fixing screws are adapted to be arranged opposite to and angled toward each other.

2. The vertebra locking and retrieving system of claim 1, wherein said horizontal fixing portion of said each of said first and second fixing screws and said bar portion of said first fixation crossbar form substantially an angle of 90 degrees.

3. The vertebral locking and retrieving system of claim 1, wherein the horizontal fixing portion and the threaded portion of each of said first and second fixing screws are integrally formed.

4. The vertebral locking and retrieving system of claim 1, further comprising:
   third and fourth fixing screws, each of which is composed of a horizontal fixing portion and a threaded portion, said third and fourth fixing screws being adapted to be fastened onto a single vertebra which is different from the single vertebra to which said first and second fixing screws are fastened;
   a second fixation crossbar including a bar portion and at least one longitudinal fixing portion located at a mid-section of the bar portion thereof, said second fixation crossbar having ends respectively fastened to the horizontal fixing portion of each of said second and third fixing screws;
   third and fourth sets of fasteners for fastening respectively the horizontal fixing portion of each of said third and fourth fixing screws to the ends of the bar portion of said second fixation crossbar; and
   a longitudinal fixation rod extending between and fastened to the at least one longitudinal fixing portion of each of said first and second fixation crossbars.

5. The vertebral locking and retrieving system of claim 4, wherein the threaded portion and the horizontal fixing portion of each of said third and fourth fixing screws form an angle ranging between 3 degrees and 30 degrees, and wherein the threaded portions of said third and fourth fixing screws are adapted to be arranged opposite to and angled toward each other.

6. A method of securing a vertebral locking and retrieving system comprising:
   providing first and second fixing screws each of which is composed of a horizontal fixing portion and a threaded portion with the threaded portion and the horizontal fixing portion of each of said first and second fixing screws forming an angle ranging between 3 degrees and 30 degrees;
   threadably securing the threaded portion of each of the first and second fixing screws onto a single vertebra with the first and second fixing screws being arranged opposite to and angled toward each other; and
   fastening a first fixation crossbar including a bar portion having first and second end portions and at least one longitudinal fixing portion located approximately at a mid-section of the bar portion to the horizontal fixing portions of said first and second fixing screws with the first end portion of the bar portion being secured to the horizontal fixing portion of said first fixing screw and the second end portion of the bar portion being secured to the horizontal fixing portion of said second fixing screw.

7. The method of securing a vertebral locking and retrieving system according to claim 6, further comprising: arranging the horizontal fixing portion of each of said first and second fixing screws and the bar portion of said first fixation crossbar at an angle of substantially 90 degrees.

8. The method of securing a vertebral locking and retrieving system according to claim 6, further comprising: respectively forming the horizontal fixing portion and the threaded portion of each of said first and second fixing screws integrally.

9. The method of securing a vertebral locking and retrieving system according to claim 6, further comprising:

providing third and fourth fixing screws each of which is composed of a horizontal fixing portion and a threaded portion;

threadably securing the threaded portion of each of the third and fourth fixing screws into a single vertebra which is different from the single vertebra to which said first and second fixing screws are fastened;

fastening a second fixation crossbar including a bar portion having first and second end portions and at least one longitudinal fixing portion located approximately at a mid-section of the bar portion to the horizontal fixing portion of said third and fourth fixing screws; and attaching a longitudinal fixation rod to the at least one longitudinal fixing portion of each of said first and second fixation crossbars.

10. The method of securing a vertebral locking and retrieving system according to claim 9, further comprising: forming the threaded portion of each of said third and fourth fixing screws at an angle ranging between 3 degrees and 30 degrees relative to a respective one of the horizontal fixing portions of said third and fourth fixing screws.

11. The method of securing a vertebral locking and retrieving system according to claim 9, further comprising: arranging the third and fourth fixing screws opposite to and angled toward each other when fastened.

* * * * *